United States Patent [19]

Lerch

[11] Patent Number: 5,449,823
[45] Date of Patent: Sep. 12, 1995

[54] COMPOUNDS AND PROCESS FOR MAKING A FLAVORANT

[75] Inventor: Konrad Lerch, Zurich, Switzerland

[73] Assignee: Givaudan-Roure Corporation, Clifton, N.J.

[21] Appl. No.: 234,095

[22] Filed: Apr. 28, 1994

[30] Foreign Application Priority Data

May 6, 1993 [CH] Switzerland ............... 1394/93

[51] Int. Cl.6 ........................... C07C 59/147
[52] U.S. Cl. ................. 562/577; 549/295; 435/146
[58] Field of Search ............ 562/577; 549/295; 435/146

[56] References Cited

U.S. PATENT DOCUMENTS 4,973,747 11/1990 Singh, Jr. et al. ............ 562/577

Primary Examiner—Paul J. Killos
Attorney, Agent, or Firm—George M. Gould; George W. Johnston; Mark E. Waddell

[57] ABSTRACT

Two optically active forms of 4-hydroxy-3-methyl-2-keto-pentanoic acid of the formula

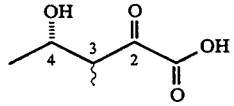

wherein carbon atom 4 has the (S)-configuration, and carbon atom 3 can have the (R)-configuration or the (S)-configuration (compound I) are made using a biotransformation process. Compound I may be manufactured by reacting 4-hydroxy-isoleucine (2S, 3R, 4S) of the formula:

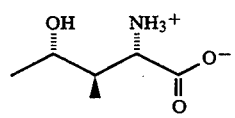

with microorganisms which have L-amino acid oxidase activity or with an L-amino acid oxidase. Compound I is a flavor precursor and may also be used as an intermediate for the production of the optically active (5S)-3-hydroxy-4,5-dimethyl-2(5H)-furanone:

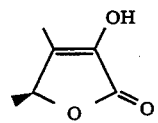

which is useful as a flavorant.

7 Claims, No Drawings

COMPOUNDS AND PROCESS FOR MAKING A FLAVORANT

BACKGROUND OF THE INVENTION

The invention concerns keto-pentanoic acid derivatives as flavorants and intermediates.

SUMMARY OF THE INVENTION

There are disclosed optically active 4S-hydroxy-3-methyl-2-keto-pentanoic acids (2-keto-3-methyl-4-hydroxy valeric acid) of the formula

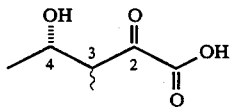   I wherein carbon atom 4 has the (S)-configuration and carbon atom 3 has either the (R)- or the (S)-configuration.

The compounds are useful as flavorants especially flavor precursors.

DETAILED DESCRIPTION

The invention is concerned with two new, optically active forms of 4-hydroxy-3-methyl-2-keto-pentanoic acid of the formula:

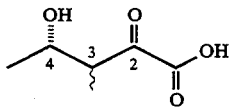   I wherein carbon atom 4 has the (S)-configuration and carbon atom 3 can have the (R)- or the (S)-configuration. These compounds may be used as flavorants, especially as flavor precursors. As used herein, the term "compound I" encompasses both of the above-described optically active forms of the compounds of formula I.

The invention is also concerned with a microbiological process for the manufacture of compound I. This process comprises reacting 4-hydroxyisoleucine (2S,3R,4S) ("L-4-hydroxyisoleucine") of the formula:

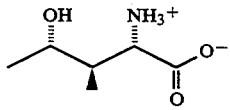   II with microorganisms which have L-amino acid oxidase (EC (Enzyme Commission [i.e. International Commission on Enyzmes] Classification) 1.4.3.2.) activity or with an L-amino acid oxidase.

The compound of formula I may also be used as intermediates for the production of the optically active (5S)-3-hydroxy-4,5-dimethyl-2(5H)-furanone of the formula

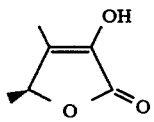   III

The racemate of compound III is an important flavorant having an extremely low threshold value (H. Sulser, M. Habegger, W. Büchi, Z. Lebensm. Unters. Forsch. (1972), 148, 215).

The present invention enables compound III to be produced from a natural raw material using a process which is considered to be natural.

Seeds of fenugreek Trigonellum foenum graecum L. are especially suitable as the raw material for compound I and, ultimately, compound III. Fenugreek seeds contain relatively large amounts (5 g/kg seeds) of free L-4-hydroxyisoleucine (L. Fowden, H. M. Pratt, A. Smith, Phytochemistry (1973), 12, 1707). Using the discovered biotransformation system in accordance with the invention, the L-4-hydroxyisoleucine present in the Trigonellum seeds can be converted in a simple manner into compound I.

This is acheived, as indicated above, by reacting L-4-hydroxyisoleucine with microorganisms which have L-amino acid oxidase (EC 1.4.3.2.) activity or with an L-amino acid oxidase itself. The reaction proceeds as follows:

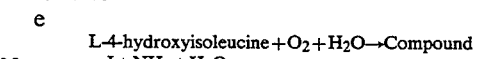

The diastereomeric forms of 2-keto-3-methyl-4-hydroxyvaleric acid (compound I) produced by the reaction may be isolated fairly easily as metal salts, such as alkali metal or alkaline earth metal salts. (e.g. sodium or potassium salts.) The free acids are very labile and cyclize spontaneously to the optically active lactone III.

A wide variety of microorganisms, such as bacteria and fungi, and algae are suitable for the biotransformation of L-4-hydroxyisoleucine into compound I.

Preferred organisms are those having high L-amino acid oxidase activity. Included in these are: (1) algae of the genus Amphiroa, Gymnogongrus etc; (2) fungi of the genus Neurospora; and (3) bacteria of the genus Proteus, Providencia, Morganella, Corynebacterium.

The following organisms—all being publicly available—are particularly well suited to perform the biotransformation:

Bacteria
  Proteus vulgaris (DSM 2140, 3265),
  Proteus mirabills (ATCC 15290),
  Providencia rettgeri (ATCC 9250),
  Morganella morganii (DSM 30117).
Fungi
  Neurospora crassa (FGSC [Fungal Genetics Stock Center, Kansas City] 988 and 2963)

Prior to the actual biotransformation, the microorganisms may be cultivated in a submersed culture on a suitable nutrient medium. Both conventional complexes and chemically defined media can be used for this purpose, provided that the choice of nutrient medium does not adversely interfere with the L-amino acid oxidase activity, which, as described herein, facilitates the biotransformation of the L-4-hydroxyisoleucine (compound II) into compound I. In addition to suitable carbon and nitrogen sources, the nutrient medium may contain inorganic salts, trace elements and free amino acids.

Sugar, preferably glucose or saccharose, may be used as the carbon source. The nitrogen source may be either inorganic compounds and/or organic compounds. Possible nitrogen sources include ammonium salts, particularly ammonium sulfate and ammonium nitrate, other nitrates, yeast extract or peptone, etc.

Usually, the nutrient medium also contains salts, for example sulfates, phosphates or chlorides, especially salts of the elements magnesium, potassium and calcium, as well as the trace elements iron, zinc, manganese, boron, cobalt, copper and molybdenum. When cultivating *Neurospora crassa*, the vitamin biotin is also added.

When added to the culture medium, the free amino acids may come from protein hydrolysates, preferably from casein and soya protein hydrolysates, or in the case of individual amino acids from corresponding fermentations. Leucine, methionine and phenylalanine are preferred.

The ratio of the aforementioned nutrients depends on the mode of fermentation and may be determined on a case-by-case basis in a manner which will be known to a person skilled in the art. For example, glucose or saccharose concentrations in the range of about 5 to 50 g/l are suitable for carrying out the process of the invention, with concentrations in the range of about 10 to 20 g/l being preferred. The ammonium sulfate or ammonium nitrate, which is the preferred nitrogen source, is incorporated in the range of about 0.03 to 5 g/l, preferably about 0.06 to 2 g/l.

The mineral salts which are used may be incorporated in the range of about 0.05 to 10 g/l, particularly about 0.1 to 5 g/l. The trace elements are incorporated in aqueous solution and are usually used in a concentration range of about 0.005 to 20 mg/l. Concentrations of about 0.01 to 5 mg/l are particularly preferred.

The protein hydrolysates which are used as the source of amino acids are incorporated in the range of about 5 to 50 g/l, preferably about 10 to 20 g/l. With respect to the addition of free amino acids such as leucine, methionine or phenylalanine, the chosen amount is may be in the range of about 0.1 to 5 g/l, preferably about 0.2 to 2 g/l.

The vitamin biotin, which is required for the cultivation of *Neurospora crassan*, may be incorporated in the range of about 1 to 20 μg/l, preferably about 2 to 5 μg/l.

The fermentation temperature depends on the microorganism which is used and usually ranges between about 10° and 50° C., particularly between about 20° and 37° C. The pH of the nutrient medium is normally about 4 to 10, preferably about 5 to 8. The preferred fermentation period, (i.e. to the completion of growth), is between about 10 and 100 hours, and is usually between about 18 and 72 hours.

After the fermentation, the cells may be mechanically separated from the nutrient medium, washed and used directly for the biotransformation. However, immobilized cells or crude extracts prepared from cells, as well as, for example, isolated, L-amino acid oxidase preparations in free or immobilized form, can also be used for the conversion of L-4-hydroxyisoleucine. Since the conversion is an oxidative process, the reaction mixture is preferably shaken intensively and/or aerated.

The isolation of the enzyme from the cells, where desired, can be carried out in a manner which will be known to a person skilled in the art. (e.g. by mechanical disintegration and purification, ion exchange chromatography, and/or adsorption chromatography, etc.)

The biotransformation is preferably carried out in a pH range of about 4 to 8, most preferably from about 5 to 7. The conversion in accordance with the invention is usually carried out at a temperature of about 10° to 40° C., preferably at 20° to 37° C. The educt L-4-hydroxyisoleucine is incorporated into the reaction solution in an amount of about 0.5 to about 5% (w/v), preferably about 1 to 2%.

The L-4-hydroxyisoleucine to enzyme ratio should be chosen so that the reaction does not require too much time. The reaction time ideally is in the range of about 6 to 24 hours. Specific preferred conditions are set forth in the examples which follow. In general, however, the optimum L-4-hydroxyisoleucine to enzyme ratio can be readily determined by means of a few simple experiments. After termination of the reaction, which can be followed by amino acid analysis, the reaction mixture is lactonized in a manner known for γ-hydroxy-acids: the reaction mixture may be acidified (for example with dilute phosphoric acid), to a pH value of about 1 to about 3, preferably about 1.5 to about 2.5, and subsequently lactonized by heating. The heat treatment may be carried out in a temperature range from about 70° to 95° C. (preferably at about 80° C.) for about 20 to 90 minutes (preferably about 30 to 60 minutes).

The resulting solution can be extracted with an organic solvent such as an ester like ethyl acetate, or an ether like methyl tert-butyl ether, according to known methods (e.g. in a counter current extraction apparatus). Subsequently, the solvent may be removed by distillation and the product taken up in a carrier which is customary in the flavor industry such as, for example, an oil, particularly peanut oil, or triethyl citrate.

The cell-free reaction mixture containing compound I, which is obtained after the biotechnological conversion of L-4-hydroxyisoleucine can also be mixed directly with a carrier such as maltodextrin or another starch derivative and dried. (for example, by spray drying.) This product can be used as a flavor precursor of compound III for the flavoring of food products which are to be subjected to a thermal treatment. A heat treatment (boiling, baking, frying, grilling, roasting, microwave treatment etc) may be carried out in a temperature range from about 80° to 250° C. for about 2 to 30 minutes. The amount of the precursor, compound I which is used can be varied, for example, between about 1 ppb and 5 ppm (in the final product).

The following Examples illustrate the present invention, but are not meant to limit its scope. The Examples were carried out as written.

EXAMPLE 1

Isolation and Characterization of
2-Keto-3-methyl-4-hydroxyvaleric Acid
(=4-Hydroxy-3-methyl-2-keto-pentanoic Acid)

(Compound I)

a) Isolation of L-4-hydroxyisoleucine from seeds of fenugreek *Trigonella foenum graecum L.*

The extraction and purification of L-4-hydroxyisoleucine was carried out according to the method described by L. Fowden et al. (*Phytochemistry* (1973), 12, 1707), which is incorporated herein by reference. From 4 kg of seeds of *Trigonella foenum graecum L.*, 12 g of purified L-4-hydroxyisoleucine were isolated (yield 62%). Purity: >97% (amino acid analysis). Optical rotation: $[\alpha]_D^{20} = +32.3°$ (c 1 (i.e. 1 g/100 ml), H$_2$O); literature value: 31.0°.

b) Biotransformation of L-4-hydroxyisoleucine with *Morganella morganii*

*Morganella morganii* (DSM No. 30117) was cultivated in nutrient medium A (Table 1) for 20 hours in a fermenter at pH 7 and a temperature of 30° C. Subsequently, the cells were centrifuged, washed with 0.02M sodium phosphate buffer (pH 7.0), resuspended in 0.05M sodium phosphate buffer pH 7.0 and the mixture was adjusted to an optical density of 20 at 650 nm (or an optical density of 0.2 after 100-fold dilution). This cell suspension was added to a shaking flask and treated with 7.7 mmol of L-4-hydroxyisoleucine per liter. After incubation for 6 hours at 30° C. on a shaking machine, the amount of L-4-hydroxyisoleucine provided had reacted completely. The cells were separated from the reaction mixture by centrifugation and the supernatant obtained was lyophilized.

TABLE 1

| Nutrient medium A | |
|---|---|
| Glucose | 10.0 g/l |
| Casein hydrolysate | 10.0 g/l |
| $Na_2HPO_4.2H_2O$ | 11.9 g/l |
| $KH_2PO_4$ | 4.5 g/l |
| $(NH_4)_2SO_4$ | 1.0 g/l |
| $MgSO_4.7H_2O$ | 0.1 g/l |
| $CaCl_2.2H_2O$ | 4 mg/l |
| $FeSO_4.7H_2O$ | 0.5 mg/l | c) Isolation of the sodium salt of 2-keto-3-methyl-4-hydroxyvaleric acid (I).

The freeze-dried residue was extracted with methanol and the sodium salt of compound I was precipitated in the usual manner by the addition of methyl tert-butylether. The novel substance exhibited the following physical properties:

| | |
|---|---|
| Melting point: | 144° C. (dec.) |
| Optical rotation: | $[\alpha]_D^{20}$: +18.49° (c 0.84 in methanol) |
| IR: | 1720 $cm^{-1}$, 1630 $cm^1$, 1390 $cm^{-1}$, 1130 $cm^{-1}$ |
| $^1$H-NMR: | $\delta$ = 4.18 ppm (2 × q), 3.18 (2 × q), 1.20 (2 × d), 1.05 (2 × d) |
| MS: | (electron spray ionization) 145.1 ($M^-$), 101.1, 57.2 313.1 ($2M^-Na^+$), 481.3 ($3M^-2Na^+$), 649.4 ($4M^-3Na^+$), 817.6 ($5M^-4Na^+$), (anion clusters). | d) Conversion of 2-keto-3-methyl-4-hydroxy-valeric acid (Compound I) into (5S)-3-hydroxy-4,5-dimethyl-2(5H)-furanone (Compound III)

840 mg of the sodium salt of compound I were dissolved in 50 ml of $H_2O$ and brought to pH 2.0 with dilute phosphoric acid. The solution was held at 85° C. for 30 minutes and, after cooling, extracted with 2×50 ml of ethyl acetate. 320 mg (yield 50%) of compound III separated after removal of the solvent. Compound III, purified by preparative thin-layer chromatography (silica gel 60), exhibited an optical rotation of: $[\alpha]_D^{20}$: 21.66° (c 1.0 in chloroform).

EXAMPLE 2

Cells of *Morganella morganii* were cultivated in a fermenter, centrifuged, washed and subsequently adjusted to an optical density of 20 (650 nm), as described in Example 1. After adding 7.7 mmol of L-4-hydroxyisoleucine per liter, the cell suspension was shaken at 30° C. in an Erlenmeyer flask. The amount of L-4-hydroxyisoleucine provided had reacted completely after 18 hours. The cells were separated from the reaction mixture by centrifugation and the clear supernatant was adjusted to pH 2.5 with dilute phosphoric acid. After heating (30 minutes, 80° C.) the solution was extracted twice with half volumes of ethyl acetate. A yellowish oil separated after removal of the solvent. Yield of compound III: 65%.

EXAMPLE 3

Cells of *Morganella morganii* were cultivated in a fermenter, centrifuged and subsequently washed with water, as described in Example 1. The cells were resuspended in 2% sodium alginate and introduced dropwise at room temperature into a stirred solution of $CaCl_2$ (2%). The immobilized cells, which separated in small beads, were washed thoroughly with water and subsequently used for the conversion of L-4-hydroxyisoleucine. For this purpose, a portion of sedimented, immobilized cells was treated with a solution of L-4-hydroxyisoleucine (11.25 mmol/l) and shaken at 30° C. in an Erlenmeyer flask. The amount of L-4-hydroxyisoleucine provided had reacted completely after 24 hours. The immobilized cells were separated from the reaction mixture over a suction filter and washed carefully with water. The clear filtrate was further treated as in Example 2. Yield of compound III: 60%.

EXAMPLE 4

*Providencia rettgeri* (ATCC 9250) was cultivated for 20 hours in nutrient medium A (Table 1) in a fermenter at pH 7 and a temperature of 30° C. Subsequently, the cells were centrifuged, washed with 0.02M sodium phosphate buffer pH 7.0 and resuspended in 0.1M sodium phosphate buffer pH 7.2 and adjusted to an optical density of 20 at 650 nm. This cell suspension was added to a shaking flask and treated with 7.7 mmol of L-4-hydroxyisoleucine per liter. After incubating at 30° C. for 16 hours on a shaking machine the added amount of L-4-hydroxyisoleucine had reacted completely. The cells were separated from the reaction mixture by centrifugation and the supernatant was treated further as in Example 2. Yield of compound III: 60%.

EXAMPLE 5

*Neurospora crassa* (FGSC 988) was cultivated for 48 hours in nutrient medium B (Table 2) in a 2 liter shaking flask at pH 6.0 and a temperature of 25° C. The mycelium was filtered through four layers of cotton wool gauze, washed well with water, freeze-dried and subsequently finely pulverized using a homogenizer. 5 g of mycelium powder were mixed with 50 ml of 0.1M sodium phosphate buffer pH 7.2 and stirred at 40° C. for 30 minutes. The insoluble cell constituents were removed by centrifugation and the clear supernatant was treated with 7.7 mmol of L-4-hydroxyisoleucine per liter. After an incubation period of 18 hours at 30° C. the amount of L-4-hydroxyisoleucine provided had reacted completely. The transformation of the resulting 4-hydroxy-ketoacid, compound I, into compound III was carried out according to the procedure described in Example 2. Yield: 60%.

TABLE 2

| Nutrient medium B | |
|---|---|
| Saccharose | 20.0 g/l |
| Sodium citrate.5 $H_2O$ | 3.0 g/l |
| $KH_2PO_4$ | 5.0 g/l |
| $(NH_4)NO_3$ | 0.08 g/l |
| $MgSO_4.7H_2O$ | 0.2 g/l |

TABLE 2-continued

| Nutrient medium B | |
|---|---|
| CaCl$_2$.2H$_2$O | 0.1 g/l |
| L-Phenylalanine | 0.73 g/l |
| ZnSO$_4$.7 H$_2$O | 5.0 mg/l |
| Fe(NH$_4$)$_2$(SO$_4$)$_2$.6H$_2$O | 1.0 mg/l |
| CuSO$_4$.5 H$_2$O | 0.25 mg/l |
| MnSO$_4$.1 H$_2$O | 0.05 mg/l |
| H$_3$BO$_3$ | 0.05 mg/l |
| Na$_2$MoO$_4$.2 H$_2$O | 0.05 mg/l |

EXAMPLE 6

The crude extract described in Example 5 was used for the covalent immobilization of L-amino acid oxidase. 50 ml of extract were dialyzed against 1.0M potassium phosphate buffer pH 7.5 and mixed with 10 g of acrylic resin pearls Eupergit ® (Röhm Pharma, Weiterstadt, Germany). This suspension was left to stand at room temperature for 24 hours and the resin was subsequently washed with 2 l of 0.1M potassium phosphate buffer pH 7.2. The immobilized enzyme preparation was reacted with L-4-hydroxyisoleucine (7.7 mmol) at 30° C. for 24 hours as described in Example 3. Separation of the immobilized enzyme from the reaction mixture was carried out by suction filtration and the supernatant was treated further as described in Example 2. The yield of compound III was 55%.

EXAMPLE 7

Maple Syrup Flavor

Two maple syrup flavors of the following composition were prepared:

| | Parts by weight | |
|---|---|---|
| | A | B |
| Peru balsam | 5 | 5 |
| Vanilla extract | 50 | 50 |
| Butyric acid (natural) | 5 | 5 |
| Furonol (natural 15%) | 10 | 10 |
| Roast base (natural) | 5 | 5 |
| Compound III (0.1% in triacetin) (according to Example 2) | — | 150 |
| Triacetin | 925 | 775 |
| | 1000 | 1000 |

A comparison of the above flavors shows that the presence of 150 parts of compound III in B confers the typical sweet, caramel-like spicy character of maple syrup to this flavor and contributes materially to the intensification of the body. This flavor can be used, for example, in a milk drink in a concentration of 0.1%.

EXAMPLE 8

| Walnut flavor | | |
|---|---|---|
| | Parts by weight | |
| | A | B |
| Cocoa shell extract | 50 | 50 |
| Vanilla extract | 10 | 10 |
| Oleic acid | 30 | 30 |
| Walnut base (natural) | 10 | 10 |
| Compound III (0.1% in triacetin) (according to Example 2) | | 120 |
| Propylene glycol | 900 | 780 |
| | 1000 | 1000 |

A comparison of the above flavors shows that the presence of 120 parts of compound III in flavor composition B confers the typical walnut flavor character to this flavor and contributes materially to the intensification of the nutty and fatty notes. This flavor can be used, for example, in a milk drink in a concentration of 0.1%.

EXAMPLE 9

HVP-free Brown Sauce

A HVP-free brown sauce of the following composition was prepared:

| Ingredient | Parts by weight |
|---|---|
| White flour | 370 |
| Beef fat | 145 |
| Modified starch | 145 |
| Yeast extract | 97 |
| Cooking salt | 80 |
| Tomato powder | 60 |
| Maltodextrin | 53.7 |
| Monosodium glutamate | 30 |
| Caramel powder | 10 |
| Curcuma | 4.5 |
| Spice mixture (Spice'N'Easy ®) (onion, garlic and rosemary extract) | 4.8 |
| | 1000 |

When the sauce was heated in the presence of the flavor precursor compound I (2 ppm), the flavor was clearly intensified in the direction of meat, bouillon, HVP and salt.

EXAMPLE 10

| Crackers | |
|---|---|
| Ingredient | Parts by weight |
| White flour | 575 |
| Vegetable fat | 150 |
| Skim milk powder | 37 |
| Powdered sugar | 15 |
| Sweetened whey powder | 10.2 |
| Yeast autolysate | 10.0 |
| Ammonium bicarbonate | 10.0 |
| Cooking salt | 10.0 |
| Sodium hydrogen pyrophosphate | 1.0 |
| White pepper | 0.4 |
| Paprika | 0.4 |
| Water | 181 |
| Compound I | 1 ppm |

When the cracker dough was baked (230° C., 10 min.) in the presence of compound I, the room flavor and the flavor of the product was intensified in a spicy, bouillon-like and herby direction.

I claim:

1. Optically active 4S-hydroxy-3-methyl-2-keto-pentanoic acids of the formula

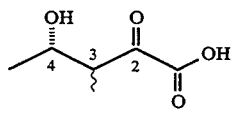

wherein carbon atom 4 has the (S)-configuration and carbon atom 3 has either the (R)- or the (S)-configuration.

2. A process for the manufacture of a compound of the formula:

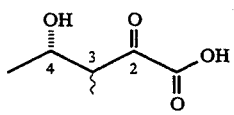

wherein carbon atom 4 has the (S)-configuration and carbon atom 3 has either the (R)- or the (S)-configuration comprising reacting L-4-hydroxyisoleucine with an L-amino acid oxidase or with a microorganism containing L-amino acid oxidase.

3. A process for the production of optically active (5S)-3-hydroxy-4,5-dimethyl-2(5H)-furanone of the formula

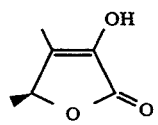

which comprises lactonizing a compound of the formula

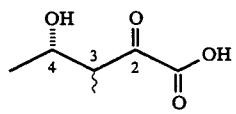

wherein carbon atom 4 has the (S)-configuration and carbon atom 3 has either the (R)- or the (S)-configuration, by acidifying a solution containing compound I and heating the acidified solution to a temperature and for a time which is sufficient to lactonize compound I.

4. A flavor precursor for use in food products subject to thermal treatment, comprising the compounds of claim 1.

5. A method for making a flavorant composition comprising the steps of:

(a) lactonizing a compound of the formula:

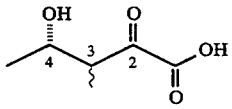

wherein carbon atom 4 has the (S)-configuration and carbon atom 3 has either the (R)- or the (S)-configuration, to form the optically active (5S)-3-hydroxy-4,5-dimethyl-2(5H)-furanone of formula

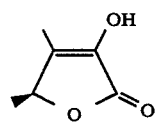

; and (b) combining compound III with a carrier.

6. The method of claim 5 wherein, prior to step (a) compound I is produced by reacting L-4-hydroxyisoleucine with an L-amino acid oxidase or a microorganism containing, L-amino acid oxidase.

7. The method of claim 6, wherein compound I is isolated prior to performing step (a).

* * * * *